(12) United States Patent
Swal et al.

(10) Patent No.: US 11,040,148 B2
(45) Date of Patent: Jun. 22, 2021

(54) DISPENSING ASSEMBLY HAVING A SYRINGE AND A NEEDLE GUARD

(71) Applicant: APTAR STELMI SAS, Villepinte (FR)

(72) Inventors: Mickaël Swal, Chauconin Neufmontiers (FR); Ghislain Fournier, La Rochelle (FR)

(73) Assignee: APTAR STELMI SAS, Villepinte (FR)

( * ) Notice: Subject to any disclaimer, the term of this patent is extended or adjusted under 35 U.S.C. 154(b) by 221 days.

(21) Appl. No.: 15/761,677

(22) PCT Filed: Sep. 20, 2016

(86) PCT No.: PCT/FR2016/052377
§ 371 (c)(1),
(2) Date: Mar. 20, 2018

(87) PCT Pub. No.: WO2017/051108
PCT Pub. Date: Mar. 30, 2017

(65) Prior Publication Data
US 2018/0344942 A1   Dec. 6, 2018

(30) Foreign Application Priority Data

Sep. 23, 2015   (FR) ..................................... 15 58966

(51) Int. Cl.
*A61M 5/32*        (2006.01)
*A61M 5/31*        (2006.01)
(52) U.S. Cl.
CPC ........... *A61M 5/3202* (2013.01); *A61M 5/321* (2013.01); *A61M 2005/3109* (2013.01)
(58) Field of Classification Search
CPC ................................................. A61M 5/3202
See application file for complete search history.

(56) References Cited

U.S. PATENT DOCUMENTS

2002/0062108 A1*  5/2002  Courteix ............. A61M 5/3202
                                                    604/198
2015/0217061 A1*  8/2015  Sadowski ........... A61M 5/3202
                                                    604/192

FOREIGN PATENT DOCUMENTS

EP        0 429 052 A1    5/1991
EP        0 976 415 A2    2/2000
(Continued)

OTHER PUBLICATIONS

International Search Report for PCT/FR2016/052377 dated Jan. 2, 2017 [PCT/ISA/210].
(Continued)

*Primary Examiner* — Nathan R Price
*Assistant Examiner* — John A Doubrava
(74) *Attorney, Agent, or Firm* — Sughrue Mion, PLLC

(57) ABSTRACT

A distribution assembly having a syringe having a body with a tip supporting a needle having a bevel, and a removable syringe needle protection device. The protection device has a flexible cap defining an inside cavity defined by a side wall and by a distal solid end wall, and when in the protection position, receiving the bevel of the needle in airtight manner. The side wall includes an annular bead provided with at least one slot extending across the bead in a longitudinal direction, the bead, when in the protection position, co-operating in airtight manner with the tip of the syringe. The cavity of the cap is dimensioned so that when the protection device is removed from the syringe, the cavity is connected to the atmosphere via the slot before the bevel of the needle becomes connected to the cavity.

5 Claims, 1 Drawing Sheet

(56) References Cited

FOREIGN PATENT DOCUMENTS

| | | |
|---|---|---|
| EP | 1 208 861 A1 | 5/2002 |
| EP | 1 964 588 A1 | 9/2008 |
| WO | 2015/052417 A1 | 4/2015 |

OTHER PUBLICATIONS

International Preliminary Report on Patentability with English Translation dated Apr. 5, 2018, in counterpart International Application No. PCT/FR2016/052377.

* cited by examiner

DISPENSING ASSEMBLY HAVING A SYRINGE AND A NEEDLE GUARD

CROSS REFERENCE TO RELATED APPLICATIONS

This application is a National Stage of International Application No. PCT/FR2016/052377, filed on Sep. 20, 2016, which claims priority from French Patent Application No. 15 58966, filed on Sep. 23, 2015.

The present invention relates to a distribution assembly comprising a syringe and a needle protection device.

Syringe needle protection devices, also referred to as needle protectors, are disclosed in particular in Documents EP 0 429 052, EP 0 976 415, EP 1 208 861, and WO 2015/052417.

Nevertheless, that type of needle protector device can present drawbacks.

Present-day needle protectors are thus likely to give rise to a drop appearing at the bevel of the needle when the needle protector is removed. That phenomenon can be troublesome, particularly in terms of losing fluid, of the integrity of the assembly, and of the drawback of needing to wipe the needle before injection, which can wipe off the silicone that is present on the needle, potentially leading to greater pain during injection. More precisely, while present-day needle protectors are being removed, they generate suction inside the internal cavity. A consequence of this suction is that suction appears at the orifice of the needle, thereby sucking up the liquid contained in the syringe. This suction, even when very small, leads to a drop appearing on the bevel at the sharp end of the needle. This phenomenon may be amplified to a greater or lesser extent by the way in which the needle cap is removed manually (at an angle, slowly, while pinching, etc.). This has the consequence of the needle being wiped, with the potential of degrading it. Furthermore, when used with an autoinjector, it is not possible to apply a drop-cleaning protocol.

An object of the present invention is to provide a distribution assembly that does not present the above-specified drawbacks.

More particularly, an object of the present invention is to provide a syringe needle protection device that guarantees that a drop will not be formed at the outlet from the needle when the protection device is removed.

Another object of the present invention is to provide a syringe needle protection device that is simple and inexpensive to fabricate and to assemble, and that is reliable in use.

The present invention thus provides a distribution assembly comprising both a syringe having a body provided with a tip supporting a needle having a bevel, and also a removable syringe needle protection device, said protection device comprising a flexible cap defining an inside cavity defined by a side wall and by a distal end wall, said end wall being solid and, when in the protection position, receiving said bevel of said needle of a syringe in airtight manner, said side wall including an annular bead provided with at least one slot extending across said annular bead in a longitudinal direction, said annular bead, when in the protection position, co-operating in airtight manner with said tip of the syringe, said cavity of said cap being dimensioned in such a manner that when said protection device is removed from said syringe, said cavity is connected to the atmosphere via said at least one slot before said bevel of the needle becomes connected to said cavity.

Advantageously, a plurality, and in particular four, slots that are regularly distributed angularly extend in the longitudinal direction across said annular bead.

Advantageously, said at least one slot is of a length shorter than the height of said tip.

Advantageously, said cap is made in compliance with the following equation:

$$X < Y + Z/2$$

where X is the distance between the point at which the bevel of the needle is closed in airtight manner and the point at which the cap and the tip are connected together in airtight manner, Y being the length of the needle between the bevel and the end surface of the tip, and Z being the height of the tip.

Advantageously, said assembly further includes a rigid shell for surrounding and containing said cap and provided with retention means for retaining said cap.

These characteristics and advantages of the present invention, and others, appear more clearly from the following detailed description, made with reference to the accompanying drawings, which are given as nonlimiting examples, and in which.

Figure 1:
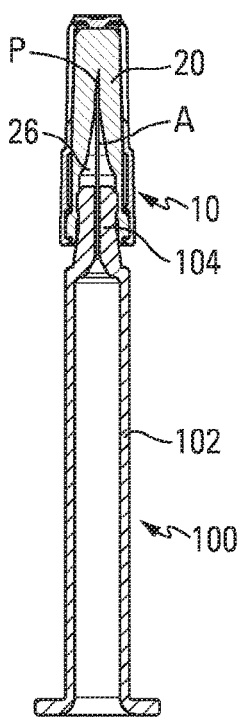
FIGS. 1 to 4 are diagrammatic longitudinal section views of a needle protection device in an advantageous embodiment of the present invention, showing four successive steps while withdrawing said needle protection device.

In the following description of the present invention, the terms "proximal" and "distal" are used relative to the rear of the syringe body, i.e. to the portion of the syringe body that is remote from the needle.

In the figures, there can be seen a protection device 10 for a syringe needle, known as a "syringe protector". The protection device 10 is for being removably assembled on a syringe 100.

Such syringe 100 comprises a syringe body 102 containing a piston (not shown), with a proximal portion 103 that is open and a distal portion 104 that supports the needle A provided with a bevel P defining the distal opening of the needle A. This distal portion 104 is also known as the "tip" of the syringe, and that is the term used below.

The needle protector 10 comprises a flexible cap 20 that defines an inside cavity 26 between a side wall 28 and a distal end wall 30. The end wall 30 is solid and of sufficient thickness to enable it to receive the bevel P of the needle A. The cap 20 is made of flexible material, typically of rubber.

Advantageously, the flexible cap 20 is a body of revolution about its longitudinal central axis. This symmetry of revolution relates to the outline of the cap 20 (the side wall 28 and the end wall 30) and also to the inside shape of the side wall 28 defining the cavity 26, except for the presence of slots and grooves, as explained below.

In the embodiment shown in the figures, in addition to the flexible cap 20, the syringe needle protector device 10 has a rigid shell 80 in which the cap 20 is received. Nevertheless, the presence of this rigid shell 80 is not essential for the present invention.

This type of shell 80 is conventionally used to provide the user of the syringe with greater protection against being pricked by the needle, by providing additional external protection that is rigid and difficult for the needle A to pierce.

This rigid shell 80 is generally in the shape of a longitudinal cylinder of circular section and it is mounted coaxially around the cap 20. The rigid shell 80 is of dimensions to enable the cap 20 to be inserted and held inside it. For this purpose, the rigid shell 80 presents an inside shape that matches substantially the outside shape of the cap 20. In order to retain the cap 20 inside of the cavity 86 of the rigid shell 80, cap retention means are provided comprising a preferably annular, inwardly directed rim 96 that forms an element, preferably a collar, projecting towards the inside.

Figure 5:
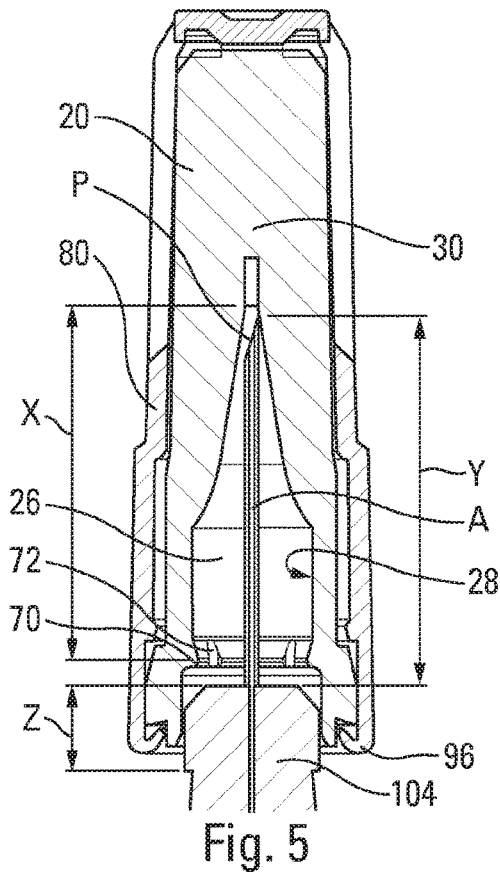
FIG. 5 is a diagrammatic longitudinal section view showing in greater detail the needle protection device in the position shown in FIG. 4.

An annular bead 70 forming an internal bulge of material is provided in the side wall 28 of the cap 20, as can be seen in particular in FIG. 5. As described in particular in document EP 1 208 861, the bead 70 is crossed by a plurality of slots 72, preferably four of them, extending in the longitudinal direction in the bead 70, these slots preferably being regularly spaced apart angularly. Naturally, it is possible to provide an arbitrary number of slots 72, which slots may be of greater or lesser depth. If there are many slots 72, then between them they divide up the bead 70 into a large number of portions, each forming a small protuberance. Likewise, the slots 72 may be of greater or smaller size. The length of each slot 72 is preferably less than the height Z of the tip 104.

As shown in FIG. 1, when the needle protector is in its protective position around the needle A, the free end of the needle A, i.e. its bevel P, is engaged in the end wall 30 of the cap 20, while the tip 104 of the syringe 100 penetrates at least in part into the housing 26 of the cap 20, and cooperates in airtight manner with said annular bead 70.

In the manner known in particular from document EP 1 208 861, the annular bead 70 co-operates with a side wall of the tip 104 of the syringe 100, thereby providing airtight closure of said cavity 26 relative to the atmosphere. When the tip 104 of the body 102 of the syringe 100 is inserted into the cavity 26 of the cap 20, the annular bead 70 is compressed by the tip 104 of the syringe, and the slots 72 therefore do not prevent the cavity 26 from being closed in airtight manner.

Figure 2:
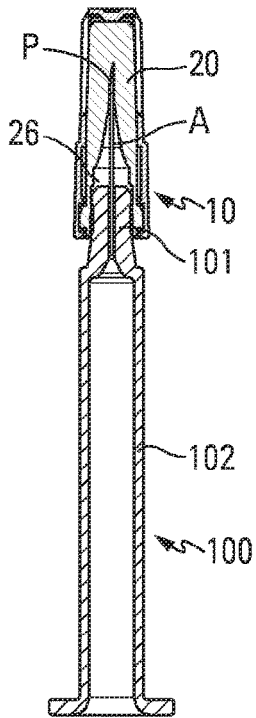
Figure 3:
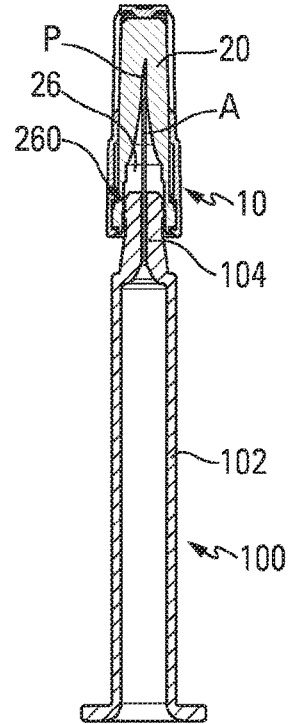
Figure 4:
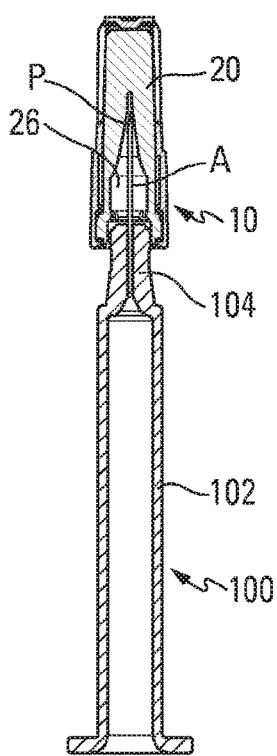

When the needle protector 10 is removed, the volume of the cavity 26 increases, as can be seen in FIGS. 1 and 2. Since said cavity 26 is closed in airtight manner both relative to the needle A and relative to the tip 104 of the syringe, suction is therefore established inside said cavity 26.

With existing needle protectors, the bevel of the needle becomes connected with said cavity while the cavity is still co-operating in airtight manner with said tip of the syringe. The suction inside the cavity then sucks in liquid through said needle.

According to the invention, the needle protector 10 is made in such a manner that while it is being removed, the cavity 26 in the cap 20 is necessarily connected to the atmosphere before the bevel P of the needle A becomes connected to said cavity 26.

To do this, the cap 20 of the needle protector 10 is preferably made in compliance with the following equation:

$$X < Y + Z/2$$

with the following definitions:
X=the distance defined between the point at which the bevel P of the needle A is closed in airtight manner, and the point at which airtight sealing is established between the cap 20 and the tip 104 of the syringe 100;
Y=the length of the needle between the bevel P and the end surface of the tip 104;
Z=the height of the tip 104.

Figure 6:
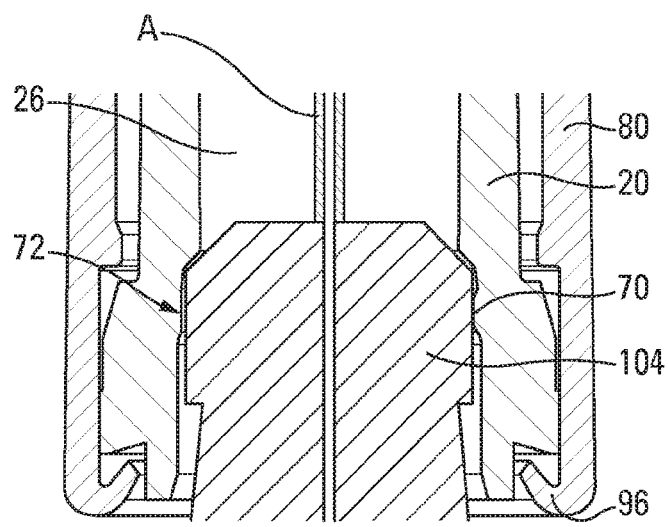
FIG. 6 is an enlarged diagrammatic longitudinal section view showing in greater detail the needle protection device in the position shown in FIG. 3.

This configuration guarantees that when the needle protector is removed, the slots 72 in the bead 70 will always connect the inside of the cavity 26 to the atmosphere (as can be seen in FIG. 6) before the bevel P of the needle A ceases to be closed in airtight manner in the end wall 30 of the cap 20. As a result, at the moment when said bevel P becomes connected with said cavity 26, the cavity will no longer be in suction, and as a result liquid will no longer be sucked through said needle A.

Although the present invention is described with reference to a particular embodiment, it should be understood that the present invention is not limited thereto, but that on the contrary, the person skilled in the art can make any useful modifications thereto without going beyond the ambit of the present invention as defined by the accompanying claims.

The invention claimed is:

1. A distribution assembly comprising both a syringe having a body provided with a tip supporting a needle having a bevel, and also a removable syringe needle protection device, said protection device comprising a flexible cap defining an inside cavity defined by a side wall and by a distal end wall, said end wall being solid and, when in a protection position, receiving said bevel of said needle of a syringe in airtight manner, said side wall including an annular bead forming an internal bulge of material, said annular bead provided with at least one slot extending across said annular bead in a longitudinal direction parallel to a central axis of the assembly, said annular bead, when in the protection position, co-operating in airtight manner with said tip of the syringe with said annular bead compressed by said tip of the syringe, wherein said cavity of said cap is dimensioned in such a manner that during removal of said protection device from the protection position on said syringe, said cavity is connected to the atmosphere via said at least one slot before said bevel of the needle becomes connected to said cavity; and
wherein said at least one slot is of a longitudinal length shorter than a longitudinal height of said tip.

2. An assembly according to claim 1, wherein said at least one slot comprises a plurality of slots that are regularly distributed angularly and extend in the longitudinal direction across said annular bead.

3. An assembly according to claim 1, wherein said cap is made in compliance with the following equation:

$$X < Y + Z/2$$

where X is the distance between a point along the central axis of the assembly corresponding to where the bevel of the needle is closed in airtight manner and a point along the central axis corresponding to where the cap and the tip are connected together in airtight manner, Y being an axial length of the needle between the bevel and an end surface of the tip, and Z being an axial height of the tip.

4. An assembly according to claim 1, further including a rigid shell surrounding and containing said cap and provided with retention means for retaining said cap.

5. The assembly according to claim 1, wherein said at least one slot comprises four slots that are regularly distributed angularly and extend in the longitudinal direction across said annular bead.

* * * * *